US009078861B2

(12) United States Patent
Caggiano et al.

(10) Patent No.: US 9,078,861 B2
(45) Date of Patent: Jul. 14, 2015

(54) USE OF A NEUREGULIN TO TREAT PERIPHERAL NERVE INJURY

(75) Inventors: Anthony O. Caggiano, Larchmont, NY (US); Anthony J. Bella, Ontario (CA); Jennifer F. Iaci, Boonton, NJ (US)

(73) Assignee: Acorda Therapeutics Inc., Ardsley, NY (US)

( * ) Notice: Subject to any disclaimer, the term of this patent is extended or adjusted under 35 U.S.C. 154(b) by 523 days.

(21) Appl. No.: 12/904,891

(22) Filed: Oct. 14, 2010

(65) Prior Publication Data

US 2011/0124561 A1  May 26, 2011

Related U.S. Application Data

(60) Provisional application No. 61/251,583, filed on Oct. 14, 2009, provisional application No. 61/252,161, filed on Oct. 16, 2009.

(51) Int. Cl.
*A61K 38/00* (2006.01)
*A61K 38/18* (2006.01)
*C07K 14/475* (2006.01)
*G01N 33/68* (2006.01)

(52) U.S. Cl.
CPC ........ *A61K 38/1883* (2013.01); *G01N 33/6893* (2013.01); *G01N 2333/4756* (2013.01); *G01N 2800/344* (2013.01)

(58) Field of Classification Search
None
See application file for complete search history.

(56) References Cited

U.S. PATENT DOCUMENTS

| | | | |
|---|---|---|---|
| 5,530,109 | A | 6/1996 | Goodearl et al. |
| 5,716,930 | A | 2/1998 | Goodearl et al. |
| 6,096,873 | A | 8/2000 | Schaefer et al. |
| 6,098,873 | A | 8/2000 | Sheffer |
| 7,037,888 | B1 | 5/2006 | Sklar et al. |
| 7,776,817 | B2 | 8/2010 | Ford |
| 7,919,582 | B2 * | 4/2011 | Schrattenholz ............... 530/329 |
| 7,973,007 | B2 | 7/2011 | Ford |
| 2002/0082229 | A1 | 6/2002 | Godowski et al. |

FOREIGN PATENT DOCUMENTS

| | | | |
|---|---|---|---|
| WO | WO-9615812 | A1 | 5/1996 |
| WO | WO-0126607 | A3 | 1/2002 |
| WO | WO 02/37968 | * | 10/2002 ............ A01N 63/00 |
| WO | WO-0189568 | A9 | 12/2002 |
| WO | WO 2005/037225 | * | 4/2005 |
| WO | WO-2009108390 | A2 | 9/2009 |
| WO | WO-2010030317 | A2 | 3/2010 |
| WO | WO-2012021818 | A2 | 2/2012 |
| WO | WO-2013149163 | A1 | 10/2013 |

OTHER PUBLICATIONS

Tokuriki and Tawflik, Current Opinion in Structural Biology 2009, 19: 596-604.*
Esper et al., Brain Res Reviews, 2006; 51: 161-175.*
Bella et al., The Journal of Urology, 185: 4S, Supplement, Monday May 16 2011; abstract 748.*
Karakiewicz et al., Urol Oncol. 1996; 2: 158-162.*
Decosterd, Pain, 2000; 87: 149-158.*
Sezen et al. ("GGF2 is Neuroprotective in a Rat Model of Cavernous Nerve Injury-Induced Erectile Dystunction", abstract #012 in J Sex Med 2012; 9(suppl 4): 186-187.*
Matsuura et al., UROLOGY, 2006; 68: 1366-1371.*
Aboseif et al. "Role of Penile Vascular Injury in Erectile Dysfunction After Radical Prostatectomy." *Br. J. Urol.* 73.1(1994):75-82.
Aitken et al. "Complications Associated With Mastectomy." *Surg. Clin. North Am.* 63.6(1983):1331-1352.
Andersson et al. "Sympathetic Pathways and Adrenergic Innervation of the Penis." *Int. J. Impot. Res.* 12.S1(2000):S5-S12.
Atlas et al. "Heregulin is Sufficient for the Promotion of Tumorigenicity and Metastasis of Breast Cancer Cells *in vivo*." *Mol. Cancer Res.* 1(2003):165-175.
Bella et al. "Nerve Growth Factor Modulation of the Cavernous Nerve Response to Injury." *J. Sex. Med.* 6.S3(2009):347-352.
Bella et al. "Upregulation of Penile Brain-Derived Neurotrophic Factor (BDNF) and Activation of the JAK/STAT Signalling Pathway in the Major Pelvic Ganglion of the Rat After Cavernous Nerve Transection." *Eur. Urol.* 52.2(2007):574-581.
Bian et al. "Neuregulin-1 Attenuated Doxorubicin-Induced Decrease in Cardiac Troponins." *Am. J. Physiol. Heart Circ. Physiol.* 297.6(2009):H1974-H1983.
Bublil et al. "The EGF Receptor Family: Spearheading a Merger of Signaling and Therapeutics." *Curr. Opin. Cell Biol.* 19.2(2007):124-134.
Buonanno et al. "Neuregulin and ErbB Receptor Signaling Pathways in the Nervous System." *Curr. Opin. Neurobiol.* 11.3(2001):287-296.
Burke et al. "When Pain After Surgery Doesn't Go Away . . ." *Transactions.* 37.Pt1(2009):318-322.
Burnett et al. "Erectile Function Outcome Reporting After Clinically Localized Prostate Cancer Treatment." *J. Urol.* 178.2(2007):597-601.
Burnett et al. "Neuromodulatory Therapy to Improve Erectile Function Recovery Outcomes After Pelvic Surgery." *J. Urol.* 176.3(2006):882-887.
Chen et al. "Recombinant Human Glial Growth Factor 2 (rhGGF 2) Improves Functional Recovery of Crushed Peripheral Nerve (a Double-Blind Study)." *Neurochem. Int.* 33.4(1998):341-351.
Chua et al. "The NRG1 Gene is Frequently Silenced by Methylation in Breast Cancers and is a Strong Candidate for the 8p Tumour Suppressor Gene." *Oncogene.* 28.46(2009):4041-4052.
çolak et al. "Comparison of Nerve Conduction Velocities of Lower Extremities Between Runners and Controls." *J. Sci. Med. Sport.* 8.4(2005):403-410.
Dail et al. "Autonomic Innervation of Reproductive Organs: Analysis of the Neurons Whose Axons Project in the Main Penile Nerve in the Pelvic Plexus of the Rat" *Anat. Rec.* 224.1(1989):94-101.
Dimachkie et al. "Peripheral Nerve Injury After Brief Lithotomy for Transurethral Collagen Injection." *Urol.* 56.4(2000):669IV-669VI.
Eichelberg et al. "Nerve Distribution Along the Prostatic Capsule." *Eur. Urol.* 51.1(2007):105-111.
Falls. "Neuregulins: Functions, Forms, and Signaling Strategies." *Exp. Cell Res.* 284.1(2003):14-30.
Fu et al. "The Cellular and Molecular Basis of Peripheral Nerve Regeneration." *Mol. Neurobiol.* 14.1-2(1997):67-116.

(Continued)

*Primary Examiner* — Christina Borgeest
(74) *Attorney, Agent, or Firm* — Mintz Levin Cohn Ferris Glovsky and Popeo, P.C.; Shovon Ashraf

(57) ABSTRACT

Embodiments of the invention are directed to use of neuregulins to prevent or treat peripheral nerve injury, to attenuate, ameliorate or avoid the loss of peripheral nerve function.

7 Claims, 6 Drawing Sheets

(56) References Cited

OTHER PUBLICATIONS

Fukazawa et al. "Neuregulin-1 Protects Ventricular Myocytes From Anthracycline-Induced Apoptosis via erbB4-Dependent Activation of PI3-Kinase/Akt." *J. Mol. Cell Cardiol.* 35.12(2003):1473-1479.
Ganzer et al. "Reply to Declan G. Murphy, Ben Dowdle and Anthony J. Costello's Letter to the Editor re: Roman Ganzer, Andreas Blana, Andreas Gaumann et al. "Topographical Anatomy of Periprostatic and Capsular Nerves: Quantification and Computerised Planimtry." Eur. Urol. 54.2(2008):353-361." *Eur. Urol.* 55.3(2009):e59-e60.
Ganzer et al. "Topographical Anatomy of Periprostatic and Capsular Nerves: Quantification and Computerised Planimtry." *Eur. Urol.* 54.2(2008):353-361.
Gassmann et al. "Aberrant Neural and Cardiac Development in Mice Lacking the ErbB4 Neuregulin Receptor." *Nature.* 378.6555(1995):390-394.
GenBank Accession No. AAB59622, May 14, 1996.
Gold et al. "Non-FK506-Binding Protein-12 Neuroimmunophilin Ligands Increase Neurite Elongation and Accelerate Nerve Regeneration." *J. Neurosci. Res.* 80(2005):56-65.
Hynes et al. "ErbB Receptors and Signaling Pathways in Cancer." *Curr. Opin. Cell Biol.* 21.2(2009):177-184.
Iaci et al. "Glial Growth Factor 2 Promotes Functional Recovery With Treatment Initiated Up to 7 Days After Permanent Focal Ischemic Stroke." *Neuropharmacol.* 59.7-8(2010):640-649.
Kaiho et al. "Nerves at the Ventral Prostatic Capsule Contribute to Erectile Function: Initial Electrophysiological Assessment in Humans." *Eur. Urol.* 55.1(2009):148-155.
Kastin et al. "Neuregulin-1-131 Enters Brain and Spinal Cord by Receptor-Mediated Transport." *J. Neurochem.* 88.4(2004):965-970.
Keast. "Plasticity of Pelvic Autonomic Ganglia and Urogenital Innervation." *Int. Rev. Cytol.* 248(2006):141-208.
Laurikainen et al. "Glial Cell Line-Derived Neurotrophic Factor is Expressed in Penis of Adult Rat and Retrogradely Transported in Penile Parasympathetic and Sensory Nerves." *Cell. Tissue Res.* 302.3(2000):321-329.
Lee et al. "Peripheral Nerve Injury and Repair." *J. Am. Acad. Orthop. Surg.* 8.4(2000):243-252.
Lee et al. "Requirement for Neuregulin Receptor erbB2 in Neural and Cardiac Development." *Nature.* 378.6555(1995):394-398.
Leungwattanakij et al. "Cavernous Neurotomy Causes Hypoxia and Fibrosis in Rat Corpus Cavernosum." *J. Androl.* 24.2(2003):239-245.
Liu et al. "Neuregulin-l/erbB-Activation Improves Cardiac Function and Survival in Models of Ischemic, Dilated, and Viral Cardiomyopathy." *J. Am. Coll. Cardiol.* 48.7(2006):1438-1447.
Meyer et al. "Multiple Essential Functions of Neuregulin in Development." *Nature.* 378(1995):386-390.
Michl et al. "Prediction of Postoperative Sexual Function After Nerve Sparing Radical Retropublic Prostatectomy." *J. Urol.* 176.1(2006):227-231.
Mulhall et al. "Erectile Function Rehabilitation in the Radical Prostatectomy Patient." *J. Sex. Med.* 7.4(2010):1687-1698.
Mulhall et al. "The Hemodynamics of Erectile Dysfunction Following Nerve-Sparing Radical Retropubic Prostatectomy." *Int. J. Impot. Res.* 8.2(1996):91-94.
Nagata et al. "Solution Structure of the Epidermal Growth Factor-Like Domain of Heregulin-α, a Ligand for p180erbB-4." *EMBO J.* 13.15(1994):3517-3523.
Nangle et al. "Impaired Cavernous Reinnervation After Penile Nerve Injury in Rats With Features of the Metabolic Syndrome." *J. Sex. Med.* 6.11(2009):3032-3044.
Özcelik et al. "Conditional Mutation of the ErbB2 (HER2) Receptor in Cardiomyocytes Leads to Dilated Cardiomyopathy." *PNAS.* 99.13(2002):8880-8885.
Rabbani et al. "Factors Predicting Recovery of Erections After Radical Prostatectomy." *J Urol.* 164.6(2000):1929-1934.
Sawyer et al. "Neuregulin-1β for the Treatment of Systolic Heart Failure." *J. Mol. Cell Cardiol.* 51.4(2011):501-505.
Sezen et al. "Immunophilin Ligand FK506 is Neuroprotective for Penile Innervation." *Nat. Med.* 7.10(2001):1073-1074.
Sharma et al. "Peripheral Nerve Injuries During Cardiac Surgery: Risk Factors, Diagnosis, Prognosis, and Prevention." *Anesth. Analg.* 91.6(2000):1358-1369.
Stewart et al. "More 'Malignant' Than Cancer? Five-Year Survival Following a First Admission for Heart Failure." *Eur. J. Heart Fail.* 3.3(2001):315-322.
Sutherland et al. "Neuroprotection for Ischaemic Stroke: Translation From the Bench to the Bedside." *Int. J. Stroke.* 7.5(2012):407-418.
User et al. "Occult Retained Penile Prosthetic Fragments in Persistent Urogenital Infections." *J. Urol.* 165.2(2001):531-533.
Vela et al. "Erectile Dysfunction After Radical Prostatectomy." *Actas Urol. Esp.* 21.9(1997):909-921. (English Abstract Only).
Wang. "Penile Rehabilitation After Radical Prostatectomy: Where Do We Stand and Where are We Going?" *J. Sex. Med.* 4.4Pt2(2007):1085-1097.
Watt-Boolsen et al. "Bioptic Strategy in Breast Cancer." *Acta Oncol.* 27.6A(1988):683-685.
Watt-Boolsen et al. "Total Mastectomy With Special Reference to Surgical Technique, Extent of Axillary Dissection and Complications." *Acta Oncol.* 27.6A(1988):663-665.
Wen et al. "Neu Differentiation Factor: A Transmembrane Glycoprotein Containing an EGF Domain and an Immunoglobulin Homology Unit." *Cell.* 69.3(1992):559-572.
Xu et al. "Extended Therapeutic Window and Functional Recovery After Intraarterial Administration of Neuregulin-1 After Focal Ischemic Stroke." *J. Cerebral Blood Flow Metab.* 26(2005):527-535.
Marchionni et al. "Glial Growth Factors are Alternatively Spliced erbB2 Ligands Expressed in the Nervous System." *Nature.* 362(1993):312-318.
Acorda Therapeutics, Inc. *Acorda Therapeutics Reports First Quarter 2014 Financial Results.* N.p., May 6, 2014. Web. May 27, 2014. http://ir.acorda.com/investors/investor-news/investor-news-details/2014/Acorda-Therapeutics-Reports-First-Quarter-2014-Financial-Results/default.aspx.
Acorda Therapeutics, Inc. *Acorda Therapeutics Reports Fourth Quarter and Full Year 2013 Financial Results.* N.p., Feb. 13, 2014. Web. May 23, 2014.
Acorda Therapeutics, Inc. *Form 10-Q (Quarterly Report), Filed May 9, 2014 for the Period Ending Mar. 31, 2014.* Web. May 27, 2014. http://acorda.q4cdn.com/bbc4e76c-a4b3-4756-be21-30a3e90b9d2f.pdf?noexit=true.
International Search Report issued in International Application No. PCT/US2013/034634 mailed Jul. 2, 2013.
Tsuruta, Hiroshi et al., "Toward the Clinical Application of Cavernous Nerve Regeneration by Alginate Gel Sponge Sheet," Japanese Journal of Urological Surgery, vol. 22(2):133-138 (2009).

* cited by examiner

USE OF A NEUREGULIN TO TREAT PERIPHERAL NERVE INJURY

This application claims priority to U.S. Provisional Application Ser. Nos. 61/251,583 filed Oct. 14, 2009 and 61/252,161 filed Oct. 16, 2009, each of which is incorporated herein by reference in its entirety.

FIELD OF THE INVENTION

The present invention relates to nerve trauma or injury. More particularly, to use of a neuregulin or functional segments thereof to prevent, treat or ameliorate peripheral nerve injury.

BACKGROUND OF THE INVENTION

Peripheral nerves are commonly injured from trauma including automobile accidents, motorcycle accidents, surgeries, knife and projectile wounds and birth injuries to both the child and mother. Common surgical causes of nerve injury include prostatectomy and mastectomy. Other common injuries during surgery are the result of long-term limb positioning or inevitable or accidental nerve compression. Following nerve injury there is a loss of sensation and/or function in the regions of the body innervated by the damaged nerve. For example, following nerve injury from prostatectomy there is commonly erectile dysfunction. Following mastectomy there is often loss of proper function of the upper extremity and/or scapula. Furthermore, following birth injury or other trauma with damage to the brachial plexus there is dysfunction in the ipsilateral limb.

Any therapy that could prevent or limit the extent of dysfunction following a nerve injury would have significant impact on current therapeutic strategies for the treatment of peripheral nerve injuries. There is a need for additional therapies and treatments for peripheral nerve injuries.

SUMMARY OF THE INVENTION

Neuregulins have been implicated as neuroprotective and neurorestorative effects in a variety of animal models of central nervous system diseases and injuries. However, prior to the present invention neuregulins had never been established as able to prevent and/or treat peripheral nerve injury. Accordingly, certain embodiments of the present invention are directed to methods of treating or ameliorating peripheral nerve injury by administering neuregulin (e.g., GGF2) or a functional segment thereof to a subject that has a peripheral nerve injury or is at risk of peripheral nerve injury.

The present invention demonstrates that neuregulin treatment of peripheral nerve injury can attenuate the loss of peripheral nerve function, ameliorate or attenuate loss of peripheral nerve function when given either before or after nerve injury, and in some instance restore peripheral nerve function. In certain embodiments, peripheral nerve injury is avoided. In certain embodiments, an existing peripheral nerve injury is eliminated. In certain embodiments, peripheral nerve injury is not totally avoided. In certain embodiments, an existing peripheral nerve injury is not totally eliminated.

The rat erectile dysfunction model is used as an in vivo system to demonstrate the effectiveness of neuregulins in treating peripheral nerve injury. In certain aspects, the invention is directed to treating erectile dysfunction resulting from peripheral nerve injury, but the current invention is not limited to only erectile dysfunction. Neuregulin can be effective as a monotherapy for any peripheral nerve injury and does not require co-treatment with natural or artificial nerve conduits or co-treatment with cellular therapies such as Schwann cells.

Certain embodiments are directed to methods of treating peripheral nerve injury comprising administering an effective amount of neuregulin to a subject having a peripheral nerve injury or a subject at risk of suffering a peripheral nerve injury. Certain embodiments are directed to methods of propylaxing or preventing peripheral nerve injury comprising administering an effective amount of neuregulin to a subject at risk of suffering a peripheral nerve injury. The term subject includes mammals, and particularly human subjects.

In certain embodiments, the peripheral nerve injury is a result of trauma including without limitation automobile accidents, motorcycle accidents, surgeries, knife and projectile wounds, and birth injuries. In certain embodiments, a peripheral nerve injury is a result of a surgery, such as a prostatectomy, mastectomy or the like. In the context of essentially any surgical intervention, peripheral nerve injury may be the direct result of tissue dissection, tissue resection and/or secondary to limb positioning and/or compression. In a particular embodiment, neuregulin is used to treat or prevent the peripheral nerve injury that would result in erectile dysfunction.

Further embodiments are directed to the treatment of erectile dysfunction resulting from surgical injury to peripheral nerves related to erectile function, such as the cavernous nerve and/or penile nerve. Cavernous nerve injury frequently occurs as the result of prostate cancer resection; this injury can cause erectile dysfunction (ED).

Current pharmaceutical interventions treat the resulting functional deficit consequent to injury by increasing the blood flow to the corpus cavernosum to facilitate penile erection. Current medical device interventions exist that treat the resulting functional deficit of the injury by increasing the volume of the penis leading to a state analogous to a normal penile erection. There are drawbacks to all existing interventions used to treat ED.

The present invention acutely protects the nerves at the time of the injury, and/or enhances patient recovery by decreasing the severity of any functional deficits.

A neuregulin 1 peptide (GGF2) was tested in a bilateral crush model in rat, which is an accepted model of cavernous nerve injury; this model has been used to test sildenifil and other ED drugs. As set forth herein, GGF2 improved functional outcomes when nerves were electrostimulated 5 weeks following injury and intercavernosal pressure (ICP) was measured.

Certain embodiments are directed to neuregulin treatment of nerve injury following mastectomy. Injury of the Long Thoracic, Intercostobrachial and Thoracodorsal nerves is common during mastectomy, although other nerves can also be damaged and neuregulin can be used to prevent or treat such injury. Neuregulin can be delivered before and/or after mastectomy to protect and restore nerve function. There are many commonly used measures of upper-limb function including strength, sensation, range of motion and reflexes—all or any of which are appropriate for determining nerve function protection or restoration. The present invention applies equally to any nerve injured in any medical or surgical procedure.

Further embodiments include neuregulin treatment of nerve injury following trauma to the brachial plexus. Brachial plexus injury is a common result of blunt force trauma, birth trauma, vehicular accident, and sporting injuries resulting in motor and sensory deficits of the affected limb. Neuregulin can be administered to a person with a brachial plexus to reduce damage and restore limb function. In situations that are foreseen, such as childbirth, a composition of the invention can be given prophylactically. Limb function can be measured by any number of accepted neurological measures of motor function, strength, sensation, range of motion and/or reflexes.

Certain aspects include administration of about 1, 2, 3, 4, 5, 6, 7, 8, 9, 10, 1-10, 1-20, 10-20, 1-30, 1-40, 1-50, 10-20, 10-30, 10, 15, 20, 25, 30, 35, 40, 50, 15-25, 15-40, 15-35, 15-50, 20-50, 20-40, 20-40, 25-35, 30-50, 30-60, 50-75, 50-100, 100, 1-100, 100-150, 150-200, 200, 1-200 μg or mg of neuregulin polypeptide or peptide based on the activity of the particular neuregulin used, and the medical context as appreciated by one of ordinary skill. Certain aspects include the administration of neuregulin prior to and/or after surgery.

In certain aspects a neuregulin may be any full-length neuregulin encoded by the NRG1, 2, 3 or 4 genes. In a further aspect a neuregulin can be any functional segment of a neuregulin polypeptide. In certain embodiments the functional segment of a neuregulin contains an EGF-like domain. In certain embodiments, a neuregulin can be any peptide from the NRG1, 2, 3 or 4 genes that binds to and activates erbB receptors. In certain embodiments a neuregulin can be any peptide modified from a wild-type peptide encoded by the NRG1, 2, 3 or 4 genes, such that the modified peptide binds to and activates erbB receptors.

Neuregulins and polypeptides containing EGF-like domains of neuregulins can be administered to subjects with a pharmaceutically-acceptable diluent, carrier, or excipient, in unit dosage form. Conventional pharmaceutical practice may be employed to provide suitable formulations or compositions to administer such compositions to patients or experimental animals. Although intravenous administration is preferred, any appropriate route of administration may be employed, for example, parenteral, subcutaneous, intramuscular, intracranial, intraorbital, ophthalmic, intraventricular, intracapsular, intraspinal, intracisternal, intraperitoneal, intranasal, aerosol, oral, or transdermal or topical administration (e.g., by applying a device or an adhesive patch carrying a formulation capable of crossing the dermis and entering the bloodstream). Therapeutic formulations may be in the form of liquid solutions or suspensions; for oral administration, formulations may be in the form of tablets or capsules; and for intranasal formulations, in the form of powders, nasal drops, or aerosols.

By "neuregulin-1," "NRG-1," "heregulin" is meant a polypeptide that binds to the ErbB receptors 1, 3 or 4, and by receptor pairing (dimerization) also to ErbB2. In one embodiment the neuregulin is encoded by the p185erbB2 ligand gene described in U.S. Pat. Nos. 5,530,109; 5,716,930; and 7,037,888, each of which is incorporated herein by reference in its entirety. In one embodiment the neuregulin is GGF2 or any subsequence thereof, or any molecule that comprises all or an active part of the sequence of GGF2.

The term "therapeutically effective amount" or an "effective amount" is intended to mean that amount of neuregulin that elicits a biological or medical response of a tissue, a system, animal or human that is being sought by a researcher, veterinarian, medical doctor or other clinician.

A therapeutic change is a change in a measured biochemical or physiological characteristic in a direction that alleviates the disease or condition being addressed, e.g., peripheral nerve injury. More particularly, an "effective amount" is an amount sufficient to decrease the symptoms associated with a medical condition or infirmity, to normalize body functions in disease or disorders that result in impairment of specific bodily functions, or to provide improvement in one or more of the clinically measured parameters of a disease or condition.

The use of the term "or" in the claims is used to mean "and/or" unless explicitly indicated to refer to alternatives only or where the alternatives are mutually exclusive." It is also contemplated that anything listed using the term "or" may also be specifically excluded from the other options being set forth.

Throughout this application, the term "about" is used to indicate that a value that is within 85%, 90%, 95% or the standard deviation of error for the device or method being employed to determine the value.

Following long-standing patent law, the words "a" and "an," in the claims or specification, denotes one or more, unless specifically noted.

In certain embodiments in accordance with the invention neuregulin is used prophylactically thereby preventing or lessening a potential injury. In certain embodiments in accordance with the invention neuregulin is used prognostically to indicate the future status of the subject. In certain embodiments in accordance with the invention neuregulin is used diagnpostically to indicate the presence or likely presence of a condition or state. In certain embodiments in accordance with the invention neuregulin is used therapeutically in order to affect a condition in some way that lessens or removes a symptom or sign of the condition or disease being treated.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to demonstrate certain aspects of the present disclosure. The invention may be better understood by reference to one of these drawings in combination with the detailed description of specific embodiments presented herein.

DETAILED DESCRIPTION OF THE INVENTION

Figure 1:
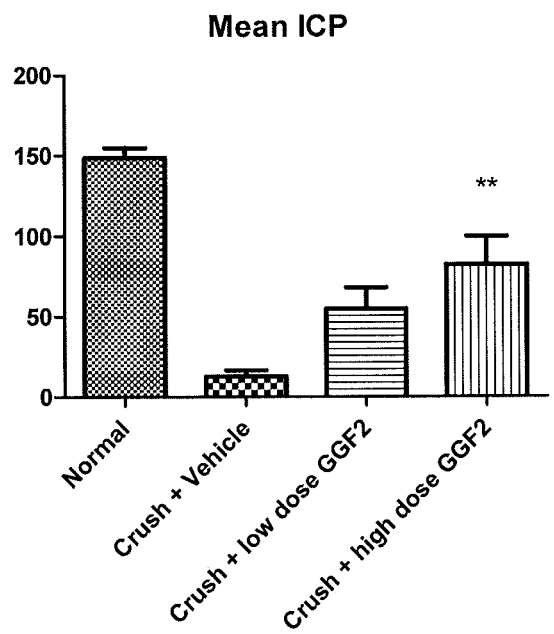
FIG. 1: Data for mean ICP change.

Injury to peripheral nerves is the common result of various events, compression, contusion, transaction, crush or stretch, caused, e.g., by trauma, accident or surgery. While the external factors leading to the nerve injury are varied, the manifestations at the nerve level have common features (For review see e.g., Lee and Wolfe, J Am Acad Orthop Surg, 8(4), p. 243, 2008). Traumatic injury of any etiology often causes damage to myelination, epineurium, perineurium, endoneurium and axons. In the mildest of cases, injury is primarily to the myelin and epineurium whereafter complete recovery occurs spontaneously within several days or weeks.

Many nerve injuries however result in disruption of endoneurium and axons and result in disruption of function that does not fully recover or recovers over a prolonged period of time.

Moreover, with a peripheral nerve injury that involves damage to an axon, there is local degeneration of that axon that occurs within hours after the injury. Over the next few days, the proximal neuron cell body and axon undergo a process known as Wallerian degeneration. Following degeneration of the axon, the myelin-producing Schwann cell dies leaving debris and inflammation. This Schwann cell death and related inflammation exacerbate nerve damage.

Unlike the central nervous system, a significant amount of regeneration can occur in peripheral nerves. The axons grow along the perineurium channels and re-innervate distal targets and Schwann cells remyelinate axons. Although there is regeneration of peripheral nerves, unfortunately, this process is not perfect; many neurons that undergo degeneration never regenerate or never find their original target and permanent dysfunction(s) result. This dysfunction can comprise loss of motor function, loss of sensory function, parathesias, loss of reflexes, rigidity, contractures or decreased range of motion.

Any therapy that could limit the extent of dysfunction following a nerve injury would have significant impact on current therapeutic strategies for the treatment of peripheral nerve injuries.

A body of literature demonstrates that neuregulins enhance the ability of neurons to regenerate through artificial conduits and function as an adjunctive therapy with cell therapies such as Schwann cell grafts. Prior to the present invention, it was not known that neuregulins alone could treat, such as by protecting and/or restoring function) in peripheral nerve injury The model employed in these studies (rat erectile dysfunction model) is a standard, accepted and well-publicized model of peripheral nerve injury. In this specific approach, the cavernous nerve is injured by forceps compression. The same compression or crush injury can be used as a model in any other peripheral nerve. In the cavernous nerve injury model the functional deficit is in erectile function. In view of the common and consistent pathophysiology of traumatic nerve injury, such cavernous nerve injury is an excellent model for prostatectomy-induced injury, as well as a general model for all traumatic peripheral nerve injuries.

Injuries to peripheral nerves induce changes within the cell bodies of sensory neurons located in the dorsal root ganglion (DRG); these changes promote survival and axonal regeneration. Under favorable conditions, for instance following a crush injury, most nerve fibers successfully regenerate. However, in many clinically relevant circumstances, traumatic or disease-induced nerve injury has a poor outcome with only a limited return of function and often with considerable delay. In such cases, neuropathic or chronic pain states can develop.

Pain is normally associated with sensory nerve injury or damage and results in guarding and immobilization of the affected area. Nociception (the neuronal signaling underlying the sensation of pain) therefore is concomitant to mechanisms for and the promotion of rapid healing, albeit triggering an unpleasant sensory and emotional experience. However, in many pathological situations, nociceptive inputs can result in functional changes that are actively detrimental to the organism.

Nerve injury results in the alteration of many of the properties of primary afferent neurons and their central connections in the spinal cord, leading to allodynia (the perception of pain from a normally innocuous stimulus), hyperalgesia (an exaggerated response to any given pain stimulus) and an expansion of the receptive field (i.e. the area that is "painful" when a stimulus is applied). The majority of chronic pain conditions arise as a result of damage to either central or peripheral nervous tissue.

Erectile Dysfunction

Impotence, or also referred to as erectile dysfunction (ED), is a common problem affecting 20 million men in the United States alone. Penile erection is a neurovascular phenomenon dependent upon both neural integrity and functional blood vessels. Upon sexual stimulation, neurotransmitters (especially nitric oxide) are released from the cavernous nerve terminals and endothelial cells. Resultant relaxation of arterial and arteriolar smooth muscles increase arterial flow. Blood trapped within the corpora cavernosa brings the penis to an erect state.

Injury to the cavernous nerve from radical pelvic surgeries, such as for prostate, bladder or rectal cancer, is one of the most common causes of iatrogenic ED in this country. ED is a major source of morbidity after radical prostatectomy. For example, despite the introduction of nerve-sparing surgical techniques, postoperative potency rates range between 30% and 80% for men who have undergone bilateral cavernous nerve-sparing procedures for organ-confined prostate cancer (Wang, *J Sex Med,* 4:1085-97, 2007).

Various neuromodulatory strategies have been investigated to date; however, there are no treatments available for either neuroprotection of the cavernous nerves prior to or at the time of injury, or treatments after injury to elicit nerve regeneration (Michl et al., *J Urol* 176:227-31, 2006; Burnett and Lue, *J Urol* 176:882-7, 2006). Despite contemporary nerve-sparing modifications to surgical and radiation therapies for pelvic malignancies there is a need for new means to preserve and restore erectile function after treatment.

Well-defined pattern of cellular changes distal to the site of damage are seen, progressing from axonal and myelin sheath degeneration, macrophage invasion, phagocytoses, and Schwann cell dedifferentiation to formation of bands of Bungner. These changes modify the injured nerve's environment and its potential for regeneration of axons. Neuronal survival is facilitated by trophic factors when axons switch from a 'transmitting' mode to growth mode, expressing proteins (GAP-43, tubulin, actin), novel neuropeptides, and cytokines New strategies enhancing growth potential are required as distal nerve stump support and neuronal capacity to regenerate are not indefinite (Fu and Gordon, *Mol Neurobiol.* 14: 67-116, 1997

Neuregulins

By "neuregulin," "neuregulin-1," "NRG-1," "heregulin," is meant a polypeptide that binds to the ErbB1, ErbB 3 or ErbB 4 receptors and by pairing (dimerization) to the ErbB2 receptor. For example, a neuregulin can be encoded by the p185erbB2 ligand gene described in U.S. Pat. Nos. 5,530,109; 5,716,930; and 7,037,888, each of which is incorporated herein by reference in its entirety; a neuregulin may also be encoded by NRG-2, 3 and 4 genes. The neuregulin can be a GGF2 or any active fragment thereof; it may also be a conservative variant of GGF2, or a molecule that comprises GGF2. In some usage in the art, the term "neuregulin" is intended to indicate only an EGF-like domain of a complete neuregulin molecule; this is also known as a "neuregulin-like" protein, peptide or polypeptide.

By "neuregulin-like" protein, peptide or polypeptide is meant a polypeptide that possesses an EGF-like domain encoded by a neuregulin gene. In one embodiment, a "neuregulin-like" protein, peptide or polypeptide produces a therapeutic effect in a subject having peripheral nerve injury or one at risk of peripheral nerve injury (e.g., patients scheduled for surgery or child birth such that there is a risk of a related peripheral nerve injury).

The GGF2 amino acid sequence (with a region comprising its EGF-like domain under lined) is: MRWRRAPRRSGR-PGPRAQRPGSAARSSPPLPLLPLLLLLG-TAALAPGAAAGNEAAPAGA SVCYSSPPSVGS-VQELAQRAAVVIEGKVHPQRRQQGALDRKAAAAAG-EAGAWGGDRE PPAAGPRALGPPAEEPL-LAANGTVPSWPTAPVPSAGEPGEEAPY-LVKVHQVWAVKAGG LKKDSLLTVRLGTWGHPAFP-SCGRLKEDSRYIFFMEPDANSTSRAPAAFRASFPPLE-TGR NLKKEVSRVLCKRCALPPQLKEMKSQE-SAAGSKLVLRCETSSEYSSLRFKWFKNGNELN RKNKPQNIKIQKKPGKSEL-RINKASLADSGEYMCKVISKLGND-SASANITIVESNATSTST TGTSHLVKCAEKEKT-FCVNGGECFMVKDLSNPSRYLCKCPNEFTGDRCQN-YVMASFYS TSTPFLSLPE (SEQ ID NO:1) (GenBank accession number AAB59622, which is incorporated herein by reference). In certain aspects of the invention, a neuregulin polypeptide or segment thereof is 75, 80, 85, 90, 91, 92, 93, 94, 95, 96, 97, 98, 99, or 100% identical or homologous to the amino acid sequence of GGF2. In certain aspects of the invention, a neuregulin-like polypeptide is 75, 80, 85, 86, 97, 88, 89, 90, 91, 92, 93, 94, 95, 96, 97, 98, 99, or 100% identical or homologous to the amino acid sequence of the EGF-like domain of GGF2.

As used herein, a "protein" or "polypeptide" refers to a molecule comprising at least ten amino acid residues. In certain embodiments the protein comprises all or part of the GGF2 polypeptide. In some embodiments, a wild-type version of a protein or polypeptide is employed, however, in some embodiments of the invention, a modified protein or polypeptide is employed to treat peripheral nerve injury. The terms "peptide," "protein" or "polypeptide" are used interchangeably herein. For convenience the term peptide is used herein to refer to amino acid sequences of any length.

A "modified peptide" refers to a peptide whose chemical structure, particularly its amino acid sequence, is altered with respect to the respective wild-type peptide. In some embodiments, a modified peptide has at least one modified amino acid. In some embodiments, a modified peptide has at least one d-amino acid. In some embodiments, a modified peptide has at least one non-naturally occurring amino acid.

Without limitation, in certain embodiments the size of a peptide (wild-type or modified) may comprise any of (or any range derivable from): 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 422, amino molecules or greater, and any range derivable therein, of a corresponding amino sequence described or referenced herein; in one embodiment such protein, polypeptide or size range is relative to GGF2. It is contemplated that polypeptides may be mutated by amino terminal or carboxy terminal truncation, rendering them shorter than their corresponding wild-type form, but also they might be altered by fusing or conjugating a heterologous protein sequence with a particular function (e.g., for targeting or localization, for purification purposes, etc.).

As used herein, an "amino acid molecule" refers to any amino acid, amino acid derivative, or amino acid mimic known in the art. In certain embodiments, the residues of the peptide molecule are sequential, without any non-amino molecule interrupting the sequence of amino molecule residues. In other embodiments, the sequence may comprise one or more non-amino molecule moieties. In particular embodiments, the sequence of residues of the peptide molecule may be interrupted by one or more non-amino molecule moieties.

Accordingly, the term "peptide" composition comprises amino acid sequences; these amino acids can be any of the 20 common amino acids in naturally synthesized proteins or any modified or unusual amino acid.

Peptide compositions may be made by any technique known to those of skill in the art, including (i) the expression of peptides through standard molecular biological techniques, (ii) the isolation of peptide compounds from natural sources, or (iii) chemical synthesis. The nucleotide as well as the peptide sequences for certain neuregulin genes have been previously disclosed, and may be found in the recognized computerized databases. One such database is the National Center for Biotechnology Information's Genbank and Gen-Pept databases (on the World Wide Web at ncbi.nlm.nih- .gov/). The coding regions for these genes may be amplified and/or expressed using the techniques disclosed herein or such techniques as would be known to those of ordinary skill in the art.

Modified peptides can include substitutional, insertional, or deletion variants. Deletion variants typically lack one or more residues of the native or wild-type molecule. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the peptide. This may include the insertion of one or more residues. Terminal additions, often called fusion proteins or fusion peptides, may also be generated. Substitutional variants typically contain the exchange of one amino acid for another at one or more sites within the peptide, and may be designed to modulate one or more properties of the peptide, with or without the loss of other functions or properties, such as binding and activation of neuregulin receptors. Substitutions may be conservative, that is, one amino acid is replaced with one of similar shape and charge. Alternatively, substitutions may be non-conservative such that a function or activity of the peptide may be affected. Non-conservative changes typically involve substituting a residue with one that is chemically dissimilar, such as a polar or charged amino acid for a nonpolar or uncharged amino acid, and vice versa.

"Conservative substitutions" are well known in the art and include without limitation, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine or leucine or methionine; serine to threonine; threonine to serine; tryptophan to tyrosine; tyrosine to tryptophan or phenylalanine; and valine to isoleucine or leucine.

It also will be understood that amino acid and nucleic acid sequences may include additional residues, such as additional N- or C-terminal amino acids, or 5' or 3' sequences, respectively, so long as the sequence meets the functional criteria set forth herein such as the maintenance of biological activity. The addition of terminal sequences particularly applies to nucleic acid sequences that may, for example, include various non-coding sequences flanking either of the 5' or 3' portions of the coding region.

Pharmaceutical Formulations

Pharmaceutical formulations of the present invention comprise an effective amount of a peptide dissolved or dispersed in a pharmaceutically acceptable carrier. The phrases "pharmaceutical or pharmacologically acceptable" refer to compositions that do not generally produce an adverse, allergic or other untoward reaction when administered to a subject, e.g., a human, as appropriate. The preparation of such pharmaceutical compositions are known to those of skill in the art in light of the present disclosure, as exemplified by Remington's Pharmaceutical Sciences, 18th Ed. Mack Printing Company, 1990, incorporated herein by reference. Moreover, for human administration purposes it will be understood that preparations should meet sterility, pyrogenicity, general safety and purity standards as required by, e.g., the USFDA Office of Biological Standards.

Moreover, as used herein "pharmaceutically acceptable carrier" includes materials such as solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as is known to one of ordinary skill in the art in view of the present disclosure. Except insofar as any conventional carrier is incompatible with an active ingredient, its use in the therapeutic or pharmaceutical compositions is contemplated.

The pharmaceuticals of the present invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, intratumorally, intramuscularly, subcutaneously, subconjunctival, intravesicularly, mucosally, intrapericardially, intraumbilically, intraocularally, orally, topically, locally, by inhalation (e.g., aerosol). Moreover, the present invention can be administered by injection, infusion, continuous infusion, localized perfusion bathing target cells directly, via a catheter, via a lavage, or by other method or any combination of the forgoing as would be known to one of ordinary skill in the art.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The pharmaceuticals may be formulated into a composition in a free base, neutral or salt form. Pharmaceutically acceptable salts include the acid addition salts, e.g., those formed with the free amino groups of a peptide composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations of such methods. In many cases, it will be preferable to include isotonic agents, such as, for example, sugars, sodium chloride or combinations thereof.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to modify the physical form of the dosage unit. For instance, tablets, pills, or capsules may be coated with shellac, sugar or both.

Sterile injectable solutions can be prepared by incorporating active compounds of the invention in the required amount in the appropriate solvent optionally with various of the other ingredients enumerated above, as called for, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques that yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

Preferably, a composition of the invention is stable under standard conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by compositions of the invention that comprise agents that delay absorption, such as, for example, aluminum monostearate, gelatin or combinations thereof.

EXAMPLES

Example 1

The Rat Model of Cavernous Nerve Injury

The rat model of cavernous nerve injury typically uses the following methodology. Rats are anesthetized with isoflurane. The animals are placed on a heating pad to maintain the body temperature at 37° C. The abdomen is shaved and scrubbed with antiseptic Clinidin solution (povidone iodine). A midline lower abdominal opening of peritoneal cavity is made, exposing both cavernous nerves and major pelvic ganglion (MPGs). Cavernous nerve injury is induced by crushing the cavernous nerve with a hemostat for two minutes per side. In the studies related to neuregulin, two neuregulin groups were treated 48 hours prior to injury.

The rat crush model provides a simple, reproducible and extremely reliable decrease of erectile function. This technique is used extensively and several studies have been published using this technique. There is no need to test erectile function after crush injury, decreased erectile function is predictable, and typically, functional testing is performed at about 5 weeks post crush-injury.

After injury to the cavernous nerve the abdominal cavity is closed in two layers with reapproximation of the abdominal muscles and fascia (absorbable suture) via 2-3 interrupted sutures. The skin is closed using a subcuticular (buried) running suture for the skin with a non-wicking (PDS or coated vicryl) suture material. Buprenorphine analgesic was given preemptively (10 minutes prior to procedure ending) and every 6-12 hours postoperatively for 48 hours for pain control.

At about 5 weeks postoperative, rats were anesthetized with Ketamine (100 mg/kg IP) and Xylazine (5 mg/kg). Cavernosal crura are exposed through the same incision and functional studies performed using a 23 G needle inserted into the left crura and connected to a software program specifically designed to measure intracavernous pressures. Prior to measurement, the cavernous nerves are stimulated with an electrode at 1.5 mA. Length of measurement procedure is approximately 15 minutes. The rats were euthanized with euthanyl-intercardiac before anesthetic recovery and tissues (cavernous nerves, MPG, penis, prostate) collected for light microscopy and molecular and histological assessments.

Figure 2:
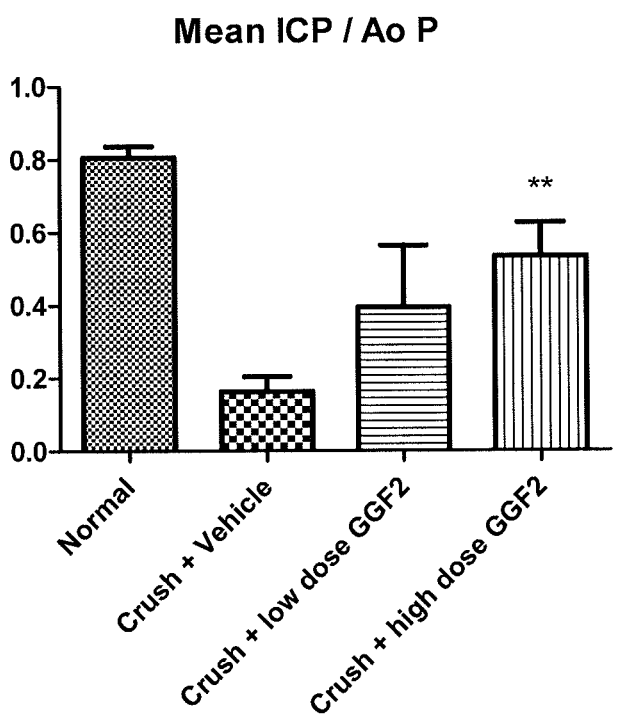
FIG. 2: Data normalized to Aortic Pressures.

As presented in the intracavernous pressures (ICP) data shown in FIG. 1, electrostimulation of the cavernous nerves 5 weeks post-injury demonstrated significant preservation of nerve and end-organ function across both neuregulin-treated groups and this was even more significant at higher doses. The data were first analyzed by non-repeated measures ANOVA with the Bonferroni t-test and significance considered at p<0.05. All results are expressed as the mean±SEM. Changes were also significantly improved when normalized to Aortic Pressures as shown in FIG. 2.

From a histological standpoint, data indicate that NRG treatment increased the number of intact nerve fibers based on the fluoro-gold retrogradely transported labeling in the MPG, and improved preservation of neuronal nitric oxide synthase and VaChT from nerve and smooth muscle tissues of the penis This indicates that there are neuroprotective and/or neuroregenerative mechanism of action. Smooth muscle apoptosis is also decreased compared to crush injury animals that do not receive any neuregulin.

Example 2

Fluoro-Gold Histology Methods

To perform this protocol, intracorporal injection of 4% fluoro-gold was performed, and at one week, Major Pelvic Ganglia (MPG) tissues were harvested and fixed in 4% paraformaldehyde, 0.1 M phosphate buffer, fixed overnight and then placed in 20% sucrose. Cryosectioning was at 20 μm thickness. Images were taken using an Infinity camera and imaging system, followed by blinded analyses for fluoro-gold enhanced cell counts. Thereafter, MPG specimen slides were randomly selected (10 per animal) and cell counts performed to determine the number of intact neurons. (See, e.g., Dail, W. G., Trujillo, D., de la Rosa, D. and Walton, G.: Autonomic innervation of reproductive organs: analysis of the neurons whose axons project in the main penile nerve in the pelvic plexus of the rat. Anat Rec, 224: 94, 1989; Laurikainen A, Hiltunen J O, Vanhatalo S, Klinge E, Saarma M: Glial cell line-derived neurotrophic factor is expressed in penis of adult rat and retrogradely transported in penile parasympathetic and sensory nerves. (Cell Tissue Res 2000, 302:321-9.)

Thus, this was a retrograde tracing protocol using fluoro-gold. Results from this protocol provided information indicating that neuregulin treatment aided regeneration and re-projection to its target (the corpora cavernosa of the penis) and/or neuroprotection of the cavernous nerves.

Accordingly, fluoro-gold was injected into a target organ, in this case the corpora of the penis. Thereafter, uptake from the end-organ nerve terminals occurred. This uptake indicated that nerve fibers were preserved and/or re-grew into the injected area. Once there is fluoro-gold uptake, the fluoro-gold is transported in a retrograde fashion in the nerve axon and the label accumulated in the original neurons of the MPG (major pelvic ganglion).

Figure 3:
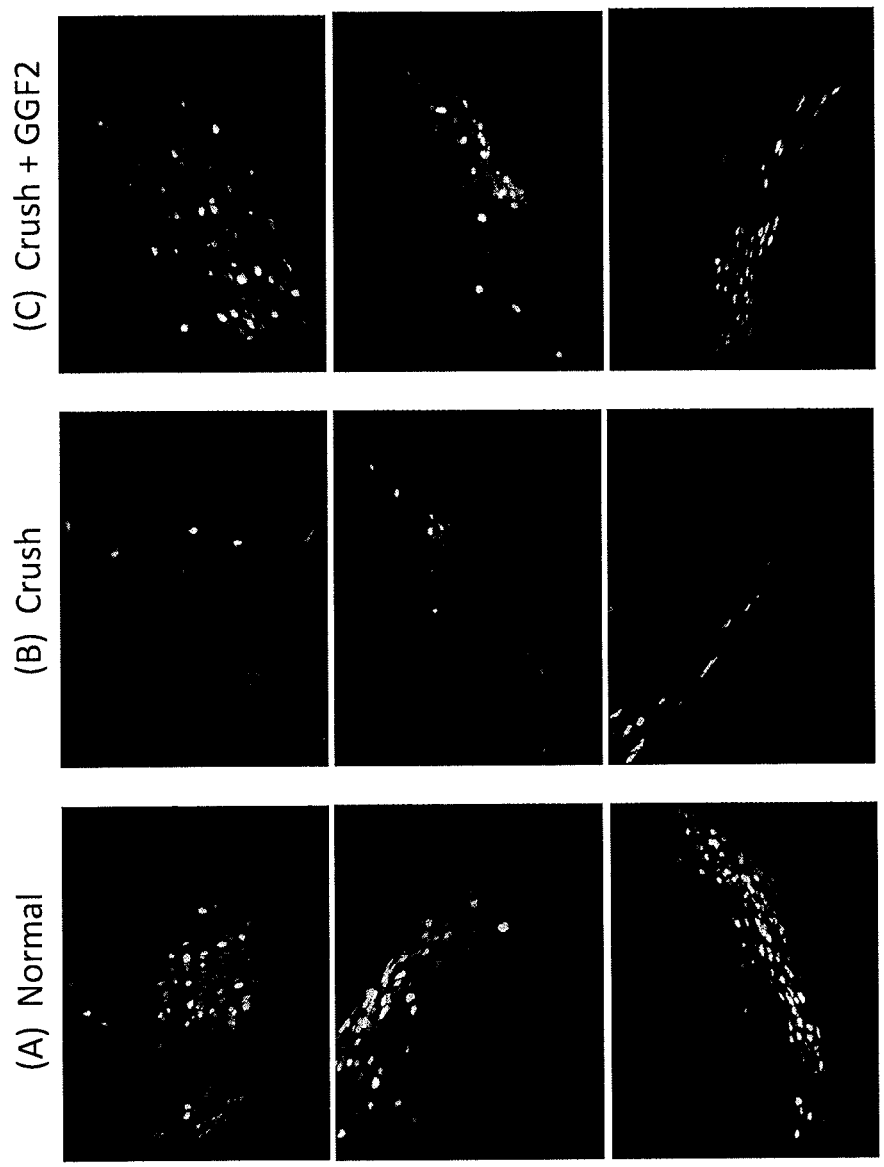
FIG. 3: Representative Fluoro-gold labeling of major pelvic ganglia (MPG) from 3 animals per treatment group ((panel A) normal, (panel B) crush, (panel C) crush+GGF2). Fluoro-gold injected into the penile tissue is transported retrogradely back through intact nerves to the cell bodies in the MPG. Panel A: Normal animals demonstrate the amount of retrograde labeling observed in the absence of nerve injury. Panel B: Crush animals demonstrate the dramatic reduction in intact nerve fibers from the injury, as the fluoro-gold label is not able to be transported all the way back to the MPG. Panel C: Crush+GGF2 animals show an increased number of fluoro-gold labeled MPG cells, indicating that there are more preserved nerve fibers present after injury as a result of GGF2 treatment.

FIG. 3 shows representative flour-gold labeling of major pelvic ganglia (MPG) from 3 animals per treatment group ((panel A) normal, (panel B) crush, (panel C) crush+GGF2). Normal animals (panel A) demonstrate the amount of retrograde labeling observed in the absence of nerve injury. Crush animals (panel B) demonstrate the dramatic reduction in intact nerve fibers from the injury, as the fluoro-gold label is not able to be transported all the way back to the MPG. Crush+GGF2 animals (panel C) show an increased number of fluoro-gold labeled MPG cells, indicating that there are more preserved nerve fibers present after injury as a result of GGF2 treatment.

Figure 4:
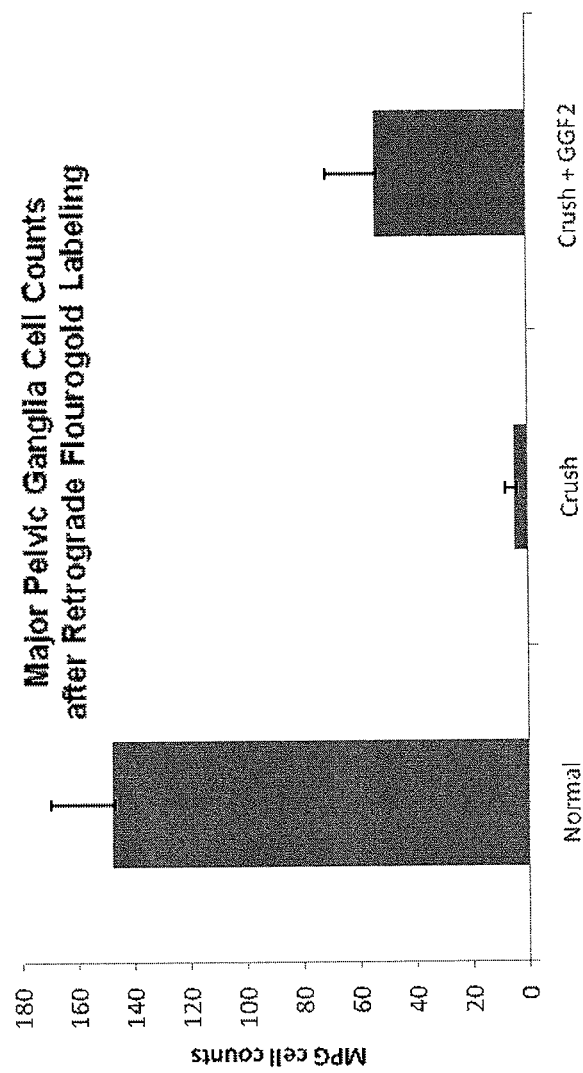
FIG. 4: Quantitation of fluoro-gold labeling in the MPG. Results showed that normal animals have a large number of cell bodies labeling in the MPG. Following a crush injury the number of labeled cells is dramatically reduced, consequent to nerve fiber damage and the resulting inability to transport retrogradely the label back to the MPG. However, GGF2 treatment improved the number of intact nerve fibers available to transport the fluoro-gold from the penile tissue to the MPG in a retrograde manner, resulting in a larger number of labeled cells.

FIG. 4 provides a quantitation of fluoro-gold labeling in the MPG. Normal animals have a large number of cell bodies labeling in the MPG. Following a crush injury the number of labeled cells is dramatically reduced, consequent to nerve fiber damage and the resulting inability to transport retrogradely the label back to the MPG. GGF2 treatment improved the number of intact nerve fibers available to transport the fluoro-gold from the penile tissue to the MPG in a retrograde manner, resulting in a larger number of labeled cells.

Example 3

Immunohistochemistry

Longitudinal cryosections of the proximal portion of the corpora were stained for nNos, VaChT. All washes were done with Tris buffer containing 1% triton-X. Tissue were blocked 1 hr with 5% normal goat serum then incubated overnight at 4 C with, respectively:
a) nNOs (Sigma; 1/1000) or
b) VaChT (Abcam; 1/150) or
c) TH (Millipore; 1/5000).

After several rinses, sections were incubated for 1 hr in goat-anti-rabbit HRP and donkey anti-goat (1/1000) then into a DAB solution containing 0.2% ammonium nickel sulfate and 0.03% hydrogen peroxide for 10 min. After the last wash, the sections were dehydrated, cleared in xylene and coverslipped in Permount (Fisher Scientific).

nNos Staining:

Nitric oxide (NO) released from the axonal endplates of the cavernous nerves within the corpora cavernosa, along with endothelial NO, causes relaxation of the smooth muscle, initiating the hemodynamic changes of penile erection as well as contributing to maintained tumescence. It is currently understood that a return to potency following injury to the cavernosal nerves is dependent, at least in part, upon axonal regeneration in the remaining neural tissues and successful functional re-innervation of the end-organ (allowing neuronal NO activation). Well-defined pathobiological changes are observed in animal model studies of the penis following cavernosal nerve compromise. These patobiological changes may range from neuropraxia to lethal axonal damage, and can include apoptosis of the smooth muscle, apoptosis of the endothelium, reduced nitric oxide synthase (NOS) nerve density, up-regulation of fibroproliferative cytokines such as transforming growth factor-beta (TGF-β), smooth muscle fibrosis or loss, or pathobiological signaling responses such as altered sonic hedgehog protein.

Additionally, a chronic absence of erection secondary to cavernosal nerve neuropraxia during the prolonged recovery phase is thought to exacerbate the potential for further cavernosal smooth muscle structural deterioration due to a failure of normal cavernosal cycling between flaccid and erect states (Bella A J, Lin G, Fandel T M, Hickling D R, Morash C, Lue T F. Nerve growth factor modulation of the cavernous nerve response to injury. J Sex Med 6 Suppl 3: 347-352, 2009.

Cavernous nNOS is a well-established marker of cavernous nerve preservation. (See, e.g., [[http://]]onlinelibrary.wiley.com/doi/10.1111/j.1464-410X.2010.09364.x/full) The results of this protocol indicated a neuroprotective and/or nerve regenerative effect following bilateral cavernous nerve injury in the rat produced according to the protocol of Example 1.

Density of staining results (representative proximal corporal sections, 5 randomly selected slides, observer blinded—based on 5 animals per group) indicated preservation of nNOS staining for subjects treated with neuregulin.

Figure 5:
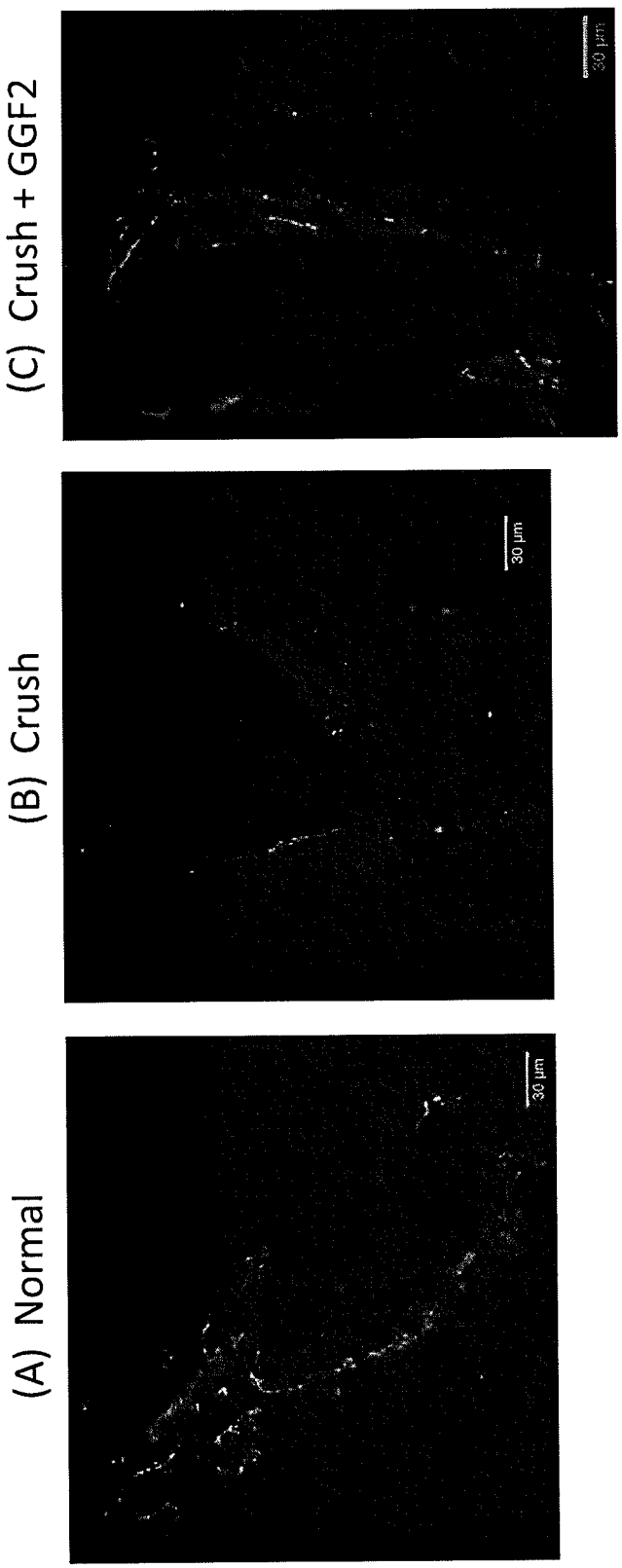
FIG. 5: Representative staining of nNos levels. Cavernous nNOS is a well-established marker of cavernous nerve preservation. Results of this work included normal tissue staining (panel A). By comparison, there was a significant loss of nNOS staining after cavernous nerve crush injury (panel B). Preserved nNOS staining of cavernous nerve endings in the penile corpora demonstrated increased rates of survival of cavernous nerves following crush injury with GGF2 treatment (panel C). Density of staining indicates preservation of nNOS staining with GGF2 treatment.

FIG. 5 provides representative staining for nNos levels. Density of staining indicates presence of nNOS. Results of this work include normal tissue staining (panel A). By comparison, there is a significant loss of nNOS staining after cavernous nerve crush injury (panel B). Preserved nNOS staining of cavernous nerve endings in the penile corpora demonstrates increased rates of survival and/or regeneration of cavernous nerves following crush injury with GGF2 treatment (panel C). Density of staining indicates preservation of nNOS staining with GGF2 treatment.

Vesicular Acetylcholine Transporter (VaChT) Staining:

Pelvic ganglion neurons that innervate the penis express nNOS and cholinergic markers, whereas sympathetic noradrenergic innervation of the penis arises largely via the sympathetic chain and does not traverse the penile nerves or pelvic ganglion. Results from this protocol provided information indicating that neuregulin treatment aided regeneration and re-projection to its target (the corpora cavernosa of the penis) and/or neuroprotection of the cavernous nerves based on intracorporal staining for vesicular acetylcholine transporter (VaChT). Although the primary etiology of post-surgical ED is neurogenic, studies in rodents have revealed that morphologic and functional changes also occur within cavernous tissue after penile nerve injury. (See, e.g., Keast J R. Plasticity of pelvic autonomic ganglia and urogenital innervation. Int Rev Cytol 2006; 248: 141-208; Andersson K E, Hedlund P, Alm P. Sympathetic pathways and adrenergic innervation of the penis. Int J Impot Res 2000; 12:55-12; Mulhall J M, Bella A J, Briganti A, McCullough A, Brock G. Erectile Function Rehabilitation in the Radical Prostatectomy Patient. J Sex Med 7(4), 1687-1698, 2010)

Density of staining results (representative proximal corporal sections, 5 randomly selected slides, observer blinded—based on 5 animals per group) indicated preservation of VaChT staining in the rats who received the GGF2.

Figure 7:
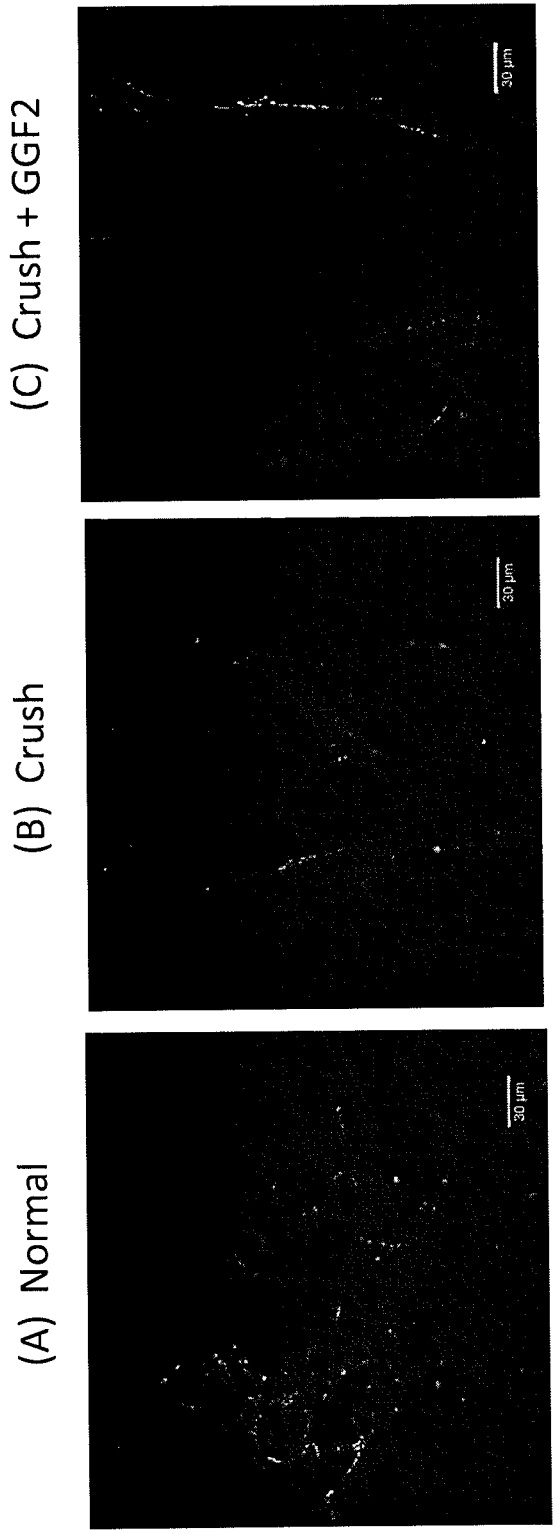
FIG. 7: Representative staining of vesicular acetylcholine transporter (VaChT). Results show normal tissue staining (panel A), and a significant loss of VaChT staining after cavernous nerve crush injury (panel B). In contrast, the preserved VaChT staining of cavernous nerve endings in the penile corpora shown in (panel C) demonstrates increased rates of survival of cavernous nerves following crush injury with GGF2 treatment (C). Density of staining shows trends towards preservation of VaChT staining with GGF2 treatment.

FIG. 7 provides representative immunohistochemical staining of vesicular acetylcholine transporter (VaChT). Density of staining indicates presence of VaChT. Results include normal tissue staining (panel A), and a significant loss of VaChT staining after cavernous nerve crush injury (panel B). In contrast, the preserved VaChT staining of cavernous nerve endings in the penile corpora shown in Panel C demonstrated increased rates of survival and/or regeneration of cavernous nerves following crush injury treated with GGF2 treatment (panel C). Density of staining shows indicates preservation of VaChT staining with GGF2 treatment.

TH Staining:

TH is a marker of adrenergic nerve fibers and is used to support nerve preservation in the corpora. The proximal portion of the corpora was cryosectioned longitudinally and stained with primary antibodies raised against the catecholamine synthesis marker, tyrosine hydroxylase (Impaired Cavernous Reinnervation after Penile Nerve Injury in Rats with Features of the Metabolic Syndrome Matthew R. Nangle, BSc, PhD, Joseph Proietto, MBBS, PhD,† and Janet R. Keast, BSc, PhD J Sex Med 2009; 6:3032-3044).

Figure 6:
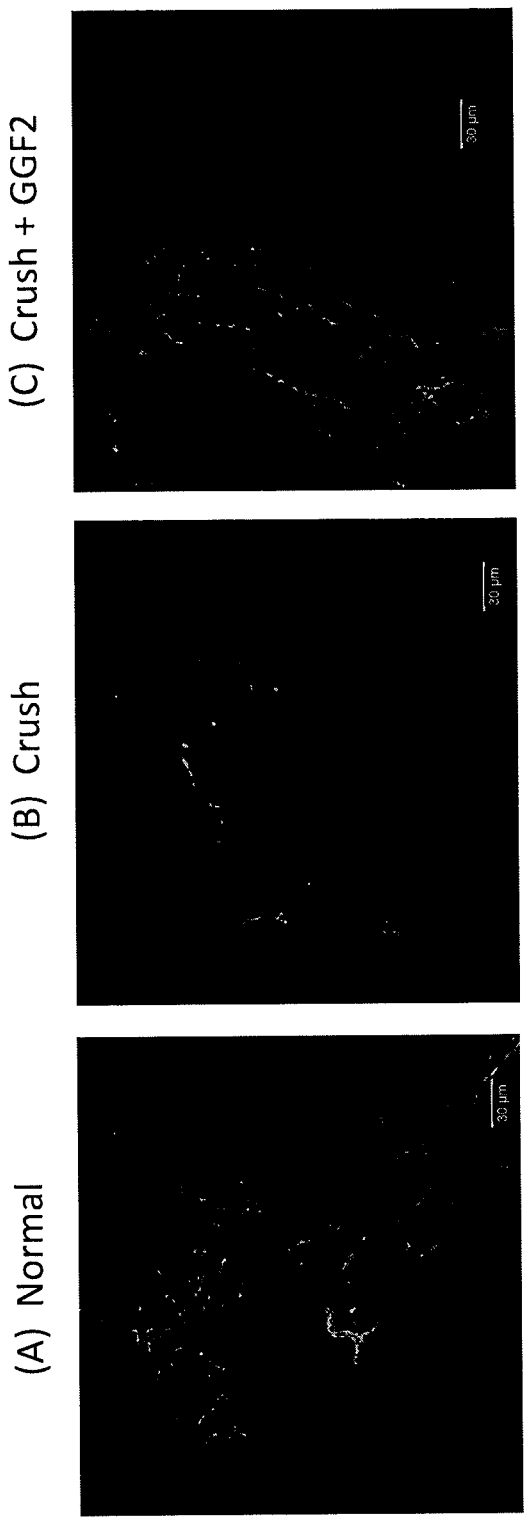
FIG. 6: Representative staining of tyrosine hydroxylase (TH) levels. The results in this figure show in panel A normal tissue staining and on panel B a significant loss of TH staining after cavernous nerve crush injury. Panel C shows preserved TH staining of cavernous nerve endings in the penile corpora; this finding corresponds to a general preservation or reestablishment of penile innervation following crush injury being produced by GGF2 treatment. Thus, the density of staining indicated preservation of TH staining with GGF2 treatment.

Density of staining results indicates presence of TH. The density of staining results actually achieved (representative proximal corporal sections, 5 randomly selected slides, observer blinded—based on 5 animals per group) indicated preservation of TH staining in animals treated with GGF2. FIG. 6 provides representative staining of tyrosine hydroxylase (TH) levels. The results include normal tissue staining (panel A) and, a significant loss of TH staining after cavernous nerve crush injury (panel B). Panel C shows preserved TH staining of cavernous nerve endings in the penile corpora best corresponds to a general increase in preservation of penile innervation following crush injury with GGF2 treatment (panel C). Density of staining shows trends towards preservation of TH staining with GGF2 treatment.

FIG. 6 provides representative staining of tyrosine hydroxylase (TH) levels. The results include normal tissue staining (panel A) and, a significant loss of TH staining after cavernous nerve crush injury (panel B). Panel C shows preserved TH staining of cavernous nerve endings in the penile corpora best corresponds to a general increase in preservation of penile innervation following crush injury with GGF2 treatment (panel C). Density of staining shows trends towards preservation of TH staining with GGF2 treatment.

Example 4

Alternative Embodiments

Peripheral nerve injury can occur in almost any surgical context. The likelihood of nerve injury is correlated with the location and extent of tissue dissection in any surgery. For example, mastectomy surgery has frequent complications resulting from peripheral nerve injury including numbness of the axilla and arm (e.g., injury to intercostobrachial nerve injury), winged scapula (injury to long thoracic nerve injury), palsy of the latissimus dorsi (injury to thoracodorsal nerve injury). (See Watt-Boolsen et al., 1988; Aitken and Minton, 1983).

Accordingly, neuregulin is used either prior to, after or both before and after mastectomy to limit injury to nerves and/or enhance recovery of peripheral nerve function. Patients scheduled to undergo mastectomy are treated about 24 hours prior to surgery with an appropriate amount of neuregulin. Optionally, patients are also treated for a period of up to about 6 weeks or more following surgery to enhance neural recovery. In alternative embodiments, patients are only treated before or only treated after surgery. As noted herein, neuregulin is used to prevent nerve injury consequent to tumor resection surgeries (prostatectomy, mastectomy, thyroidectomy, etc). It is noted that neuregulins have been implicated as promoters and as suppressors of tumor cell formation and growth (Atlas et al., 2003; Chua et al., 2009). Neuregulin treatment may or may not be contraindicated in patients with certain tumors. Neuregulins are used in patients with erbB positive tumors only when sufficient safety studies demonstrate that neuregulins do not enhance growth of such tumor.

Moreover, treatment of nerve injury from surgery is not limited to mastectomy and prostatectomy. Nerve injury frequently occurs in any surgery involving significant dissection and/or resection. These surgeries may include but are not limited to upper limb surgery, hand surgery, knee surgery/replacement, hip surgery/replacement, elbow surgery/replacement, neck dissection for arterial and venous surgery, thyroid surgery, tonsillectomy, hand and foot surgery. Peripheral nerve injury is common with pelvic, abdominal surgery and colorectal surgery. Nerve injury also occurs with oral and facial surgeries.

In addition to direct injury to nerves through dissection and resection in surgery, nerve injury frequently results from compression or stretching of nerves during surgery due to positioning of the patient, compression on contact points or from drapes, restraints, clips, tape or any other object that may compress tissue. These may be inevitable results of the surgery or the result of improper technique. No matter what the setting or etiology of peripheral nerve injury, neuregulins are found to prevent and/or treat such injury.

In humans, clinical trials demonstrate efficacy of NRG for the prevention and treatment of peripheral nerve injury with data from assessing sensory and/or motor function of frequently affected nerve regions in patients that are treated with neuregulin or with a placebo control. For example, numbness of the axilla may be tested by standard neurological methods of sensory function including tests of allodynia, hyperalgesia, sensory threshold or acuity (two-point discrimination). These methods are standard in the field. Patients are followed for a period of several months after surgery and statistical comparisons made between groups of patients treated with neuregulin and those treated with a control. Pursuant to these trails, NRG treatment before and/or after a surgical event are found to prevent and/or treat peripheral nerve injury evaluated.

Trials analogous to the foregoing also assess in a similar fashion motor strength, range of motion and coordination. Pursuant to these trials, NRG treatment before and/or after a surgical event are found to prevent and/or treat peripheral nerve injury that results in impairment in one or more of motor strength, range of motion or coordination.

What is claimed is:

1. A method of treating an erectile dysfunction resulting from a peripheral nerve injury comprising administering an effective amount of a glial growth factor 2 (GGF2) polypeptide comprising the sequence of SEQ ID NO: 1 to a subject at risk of suffering a peripheral nerve injury or to a subject having an existing peripheral nerve injury, wherein the peripheral nerve injury is the result of a surgical procedure.

2. The method of claim 1, wherein the GGF2 is administered prior to a surgical procedure.

3. The method of claim 1, wherein the surgical procedure is a prostate cancer surgery.

4. The method of claim 3, wherein the prostate cancer surgery is a prostatectomy.

5. The method of claim 1, wherein the subject is at risk of suffering a peripheral nerve injury.

6. The method of claim 1, wherein the subject has an existing peripheral nerve injury.

7. The method of claim 1 or 2, wherein the peripheral nerve injury is a cavernous nerve injury.

* * * * *

SEQUENCE LISTING

```
<160> NUMBER OF SEQ ID NOS: 1

<210> SEQ ID NO 1
<211> LENGTH: 422
<212> TYPE: PRT
<213> ORGANISM: Homo sapiens

<400> SEQUENCE: 1

Met Arg Trp Arg Arg Ala Pro Arg Arg Ser Gly Arg Pro Gly Pro Arg
1               5                   10                  15

Ala Gln Arg Pro Gly Ser Ala Ala Arg Ser Ser Pro Pro Leu Pro Leu
                20                  25                  30

Leu Pro Leu Leu Leu Leu Leu Gly Thr Ala Ala Leu Ala Pro Gly Ala
            35                  40                  45

Ala Ala Gly Asn Glu Ala Ala Pro Ala Gly Ala Ser Val Cys Tyr Ser
        50                  55                  60

Ser Pro Pro Ser Val Gly Ser Val Gln Glu Leu Ala Gln Arg Ala Ala
65                  70                  75                  80

Val Val Ile Glu Gly Lys Val His Pro Gln Arg Arg Gln Gln Gly Ala
                85                  90                  95

Leu Asp Arg Lys Ala Ala Ala Ala Ala Gly Glu Ala Gly Ala Trp Gly
                100                 105                 110

Gly Asp Arg Glu Pro Pro Ala Ala Gly Pro Arg Ala Leu Gly Pro Pro
            115                 120                 125

Ala Glu Glu Pro Leu Leu Ala Ala Asn Gly Thr Val Pro Ser Trp Pro
        130                 135                 140

Thr Ala Pro Val Pro Ser Ala Gly Glu Pro Gly Glu Glu Ala Pro Tyr
145                 150                 155                 160

Leu Val Lys Val His Gln Val Trp Ala Val Lys Ala Gly Gly Leu Lys
                165                 170                 175

Lys Asp Ser Leu Leu Thr Val Arg Leu Gly Thr Trp Gly His Pro Ala
                180                 185                 190

Phe Pro Ser Cys Gly Arg Leu Lys Glu Asp Ser Arg Tyr Ile Phe Phe
            195                 200                 205

Met Glu Pro Asp Ala Asn Ser Thr Ser Arg Ala Pro Ala Ala Phe Arg
        210                 215                 220

Ala Ser Phe Pro Pro Leu Glu Thr Gly Arg Asn Leu Lys Lys Glu Val
225                 230                 235                 240

Ser Arg Val Leu Cys Lys Arg Cys Ala Leu Pro Pro Gln Leu Lys Glu
                245                 250                 255

Met Lys Ser Gln Glu Ser Ala Ala Gly Ser Lys Leu Val Leu Arg Cys
                260                 265                 270

Glu Thr Ser Ser Glu Tyr Ser Ser Leu Arg Phe Lys Trp Phe Lys Asn
            275                 280                 285
```

```
                                -continued

Gly Asn Glu Leu Asn Arg Lys Asn Lys Pro Gln Asn Ile Lys Ile Gln
    290                 295                 300

Lys Lys Pro Gly Lys Ser Glu Leu Arg Ile Asn Lys Ala Ser Leu Ala
305                 310                 315                 320

Asp Ser Gly Glu Tyr Met Cys Lys Val Ile Ser Lys Leu Gly Asn Asp
                325                 330                 335

Ser Ala Ser Ala Asn Ile Thr Ile Val Glu Ser Asn Ala Thr Ser Thr
            340                 345                 350

Ser Thr Thr Gly Thr Ser His Leu Val Lys Cys Ala Glu Lys Glu Lys
        355                 360                 365

Thr Phe Cys Val Asn Gly Gly Glu Cys Phe Met Val Lys Asp Leu Ser
    370                 375                 380

Asn Pro Ser Arg Tyr Leu Cys Lys Cys Pro Asn Glu Phe Thr Gly Asp
385                 390                 395                 400

Arg Cys Gln Asn Tyr Val Met Ala Ser Phe Tyr Ser Thr Ser Thr Pro
                405                 410                 415

Phe Leu Ser Leu Pro Glu
            420
```